United States Patent
Burman et al.

(10) Patent No.: US 11,257,591 B2
(45) Date of Patent: Feb. 22, 2022

(54) TRANSDERMAL OPTICAL DETECTION OF CARDIAC BIOMARKERS

(71) Applicant: RCE Technologies, Inc., Decatur, GA (US)

(72) Inventors: Atandra Burman, Decatur, GA (US); Jitto Titus, Acworth, GA (US)

(73) Assignee: RCE TECHNOLOGIES, INC., Decatur, GA (US)

( * ) Notice: Subject to any disclaimer, the term of this patent is extended or adjusted under 35 U.S.C. 154(b) by 123 days.

(21) Appl. No.: 16/597,933

(22) Filed: Oct. 10, 2019

(65) Prior Publication Data

US 2020/0118679 A1    Apr. 16, 2020

Related U.S. Application Data (60) Provisional application No. 62/744,688, filed on Oct. 12, 2018.

(51) Int. Cl.
*G16H 40/67* (2018.01)
*A61B 5/1455* (2006.01)
(Continued)

(52) U.S. Cl.
CPC ........... *G16H 40/67* (2018.01); *A61B 5/0075* (2013.01); *A61B 5/02007* (2013.01);
(Continued)

(58) Field of Classification Search
CPC .............. A61B 5/0075; A61B 5/02007; A61B 5/14546; A61B 5/1455; A61B 5/7264;
(Continued)

(56) References Cited

U.S. PATENT DOCUMENTS

| 9,983,129 | B2 | 5/2018 | Titus | |
|---|---|---|---|---|
| 2009/0287076 | A1 * | 11/2009 | Boyden | A61B 5/0059 600/407 |
| 2018/0220892 | A1 * | 8/2018 | Klubben, III | A61B 5/1455 |

FOREIGN PATENT DOCUMENTS

| AU | 2012200332 A1 * | 2/2012 | ............. A61B 5/155 |
|---|---|---|---|
| AU | 2014307691 A1 * | 3/2016 | ............. G16H 50/20 |

OTHER PUBLICATIONS

Giannitsis, et al. Risk stratification in pulmonary embolism based on biomarkers and echocardiography. Circ. 112:1520-1521. (Year: 2005).*

(Continued)

*Primary Examiner* — Patrick Fernandes
*Assistant Examiner* — Liam A Wallace
(74) *Attorney, Agent, or Firm* — Cantor Colburn LLP (57) ABSTRACT

As described herein, a system includes an optical sensor, and a controller that detects progression of obstructive coronary artery disease using a sensor signal from the optical sensor. For example, the system is used for detecting an occlusion in a cardiovascular system of a user. A computer-implemented method for detecting the occlusion includes generating a light within a predetermined spectral range, the light directed towards a reflective element at a predetermined angle. The method further includes receiving a reflected light caused by a reflection of the light off of a reflecting element that is in contact with the user's epidermis. The method further includes detecting a concentration of a predetermined biomarker in a biofluid in the cardiovascular system based on variations in amplitude of the reflected light. The method further includes determining an occlusion in the cardiovascular system based on the concentration of the predetermined biomarker.

20 Claims, 4 Drawing Sheets

(51) Int. Cl.
 *A61K 35/12* (2015.01)
 *A61K 31/202* (2006.01)
 *A61B 5/00* (2006.01)
 *A61B 5/02* (2006.01)
 *A61B 5/145* (2006.01)
 *G02B 6/032* (2006.01)
 *G01N 21/65* (2006.01)

(52) U.S. Cl.
 CPC ........ *A61B 5/1455* (2013.01); *A61B 5/14546* (2013.01); *A61B 5/7264* (2013.01); *A61K 31/202* (2013.01); *A61K 35/12* (2013.01)

(58) Field of Classification Search
 CPC ...... G16H 40/67; A61K 31/202; A61K 35/12; G02B 6/032; G02B 6/2856; G02B 6/2821; G02B 6/2551; G01N 21/65; G01N 21/658; G01N 2201/0846; G01N 2201/08; G01N 2201/0612
 See application file for complete search history.

(56) References Cited

OTHER PUBLICATIONS

Azzazy, et al. Unbound Free Fatty Acids and Heart-Type Fatty Acid-Binding Protein: Diagnostic Assays and Clinical Applications. Clinical Chemistry, vol. 52, Issue 1, Jan. 1, 2006, pp. 19-29. (Year: 2006).*

Patel et al., "Ischemia-Driven Revascularization: Demonslialing and Delivering a Mature Procedure in a Mature Way," Circulation: Cardiovascular Quality and Outcomes, vol. 6, Issue 3. May 2013, pp. 250-252.

Yang, et al., "A Clinical Model to Identify Patients With High-Risk Coronary Artery Disease," JACC: Cardiovascular Imaging, vol. 8, No. 4. Apr. 2015, pp. 427-434.

* cited by examiner

TRANSDERMAL OPTICAL DETECTION OF CARDIAC BIOMARKERS

CROSS-REFERENCE AND PRIORITY

This application claims priority to U.S. Provisional Application No. 62/744,688, filed on Oct. 12, 2018, the contents of which are included herein in entirety.

BACKGROUND

The present application is generally related to transdermal optical detection of specific proteins, particularly which are in bodily fluids and which are detected substantially in real time as the fluids are interrogated through the skin by a sensor device to determine indications of progression of obstructive coronary artery disease.

Identifying the progression of obstructive coronary artery disease early and treating the disease promptly significantly improves clinical outcomes for a user thereby providing the user with the ability to seek medical intervention before there is irreversible damage. Typically, irreversible myocardial damage occurs in the first 30 to 90 minutes of coronary occlusion. Providing an intervention, such as revascularization within two hours or less of occlusion has the greatest chance to save the myocardium. Even in cases of ST elevation MI (STEMI), which is a severe type of myocardial infarcts (MI), rapid restoration of blood supply after onset of symptoms can determine the short and long term outcomes. Thus, prompt diagnosis and treatment are important to increasing the odds of a better outcome for the user and accordingly, it is desirable to detect obstructive coronary artery disease at the earliest.

SUMMARY

Described herein are techniques for using Attenuated Total Reflection Infrared Spectroscopy (ATR-IR) for noninvasively detecting particular predetermined biomarkers in bodily fluid through the skin to determine indications of myocardial infarcts (MI). For example, ATR-IR is used to detect the change in predetermined characteristic peaks associated with presence of a particular biomarker, such as a protein that is specifically released into the blood stream and consequently, interstitial fluids. The changes in the characteristic peaks are monitored by monitoring and measuring amplitude of absorption of light reflected from a user's epidermis.

As described herein, a system includes an optical sensor, and a controller that detects progression of obstructive coronary artery disease using a sensor signal from the optical sensor. For example, the system is used for detecting an occlusion in a cardiovascular system of a user. The controller is coupled with the optical sensor to receive a sensor signal from the optical sensor. The controller detects a predetermined biomarker in a biofluid in a vessel that is being monitored by the optical sensor in a noninvasive manner, the predetermined biomarker detected using reflected light in a predetermined spectral range. The controller further detects presence of an occlusion in the vessel based on the detection of the predetermined biomarker in the biofluid.

A computer-implemented method for detecting the occlusion includes generating a light within a predetermined spectral range, the light directed towards an internal reflective element at a predetermined angle. The method further includes receiving a reflected light caused by a reflection of the light off of a reflecting element that is in contact with the user's epidermis. The method further includes detecting a concentration of a predetermined biomarker in a biofluid in the cardiovascular system based on variations in amplitude of the reflected light. The method further includes determining an occlusion in the cardiovascular system based on the concentration of the predetermined biomarker.

According to one or more embodiments, a computer program product comprising a non-transitory memory having computer executable instructions stored thereon, the computer executable instructions when executed by a processing unit causes the processing unit to perform a method for detecting an occlusion in a cardiovascular system of a user. The method includes generating a light within a predetermined spectral range, the light directed towards an internal reflective element at a predetermined angle. The method further includes receiving a reflected light caused by a reflection of the light off of a reflecting element that is in contact with the user's epidermis. The method further includes detecting a concentration of a predetermined biomarker in a biofluid in the cardiovascular system based on variations in amplitude of the reflected light. The method further includes determining an occlusion in the cardiovascular system based on the concentration of the predetermined biomarker.

These and other advantages and features will become more apparent from the following description taken in conjunction with the drawings.

DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost

DETAILED DESCRIPTION

As used herein the terms module and sub-module refer to one or more processing circuits such as an application specific integrated circuit (ASIC), an electronic circuit, a processor (shared, dedicated, or group) and memory that executes one or more software or firmware programs, a combinational logic circuit, and/or other suitable components that provide the described functionality. As can be appreciated, the submodules described below can be combined and/or further partitioned.

Taking a look at the current state of the art in surveillance of coronary heart diseases, such as obstructive coronary artery disease, the conventionally used cardiac biomarker tests are based on expensive biological assays that include intrusive blood draws. Moreover, the continuity in data is absent which can be crucial in determining the rise and fall of the biomarker levels. Other tests depend on tagging or labeling the protein with fluorescent nanoparticles that adds another level of complexity in sample preparation. Also used are 12 lead electrocardiography (ECG) machines, which are not portable and mostly available in hospital settings. Additional techniques include using Holter machines, which have no real time prediction capability to forewarn an impending heart attack. Alternatively, techniques include monitoring systems that detect arrhythmias by measuring RR intervals (intervals between successive heartbeats), which cannot detect impending heart attacks because lethal arrhythmias are presented after the start of the attack. Existing techniques also include using implantable devices that can monitor ST-elevation or depression in an ECG waveform and can provide a warning based on the detection(s). The use of implantable devices requires surgery and caters only to the high risk population, where such an invasive procedure is deemed necessary. Accordingly, a technical problem exists for an accurate early warning system for heart attack and sudden cardiac death. The technical solutions described herein address such technical problem by facilitating detection of a heart attack based on detection of progression of obstructive coronary artery disease using one or more sensors that are external (not implanted) and continuously monitoring signals from the sensors. The technical solutions described herein, in one or more examples, facilitate scanning a subject in a non-invasive manner to predict if the subject can have a cardiac health problem, such as a heart attack. For example, the detection of the progression of obstructive coronary artery disease can be used to diagnose and monitor acute coronary syndrome (ACS), which includes STEMI, non-ST-elevation ACS (NSTE-ACS), and chronic coronary syndrome (CCS). Typically, stable angina (i.e. chronic pain) is a symptom of chronic coronary syndrome, which in turn is a possible diagnosis for obstructive coronary artery disease. The technical solutions described herein facilitate monitoring and identifying progression of obstructive coronary artery disease. The technical solutions described herein monitor chronic stable plaques that can grow/dislodge and lead to ACS, which includes the life threatening STEMI, as well as high risk cases in NSTE-ACS (NSTEMI, Unstable angina), and other such cases.

The technical solutions described herein, in one or more examples, include a cardiac monitoring device that monitors the subject by continuously scanning the subject. The continuous monitoring is performed by scanning the subject at a predetermined frequency. The cardiac monitoring device can have a wearable form in such cases. The cardiac monitoring device includes one or more sensors (for example, optical sensors) that transdermally scan for one or more cardiac biomarkers (for example, Troponin I, FABP3 etc.) in bodily fluids (for example, blood) of the subject. The scanning is performed non-invasively while the subject is wearing the cardiac monitoring device and performing day-to-day activities. The cardiac monitoring device may be worn on the wrist, chest, under the armpit, or any other body part of the subject.

Alternatively, or in addition, the cardiac monitoring device is not a wearable device, rather a device that receives a sample of bodily fluids from the subject. The cardiac monitoring device scans and analyzes the received sample to detect any cardiac problem with the subject. For example, the cardiac monitoring device receives the sample with the subject placing his/her body part (for example, hand) on/next to the cardiac monitoring device. Alternatively, or in addition, one or more leads of the cardiac monitoring device are placed on the subject's body to interrogate the sample in a noninvasive manner. Alternatively, or in addition, one or more surfaces of the cardiac monitoring device are placed next to the subject's body, for example, next to the subject's chest.

In one or more examples, the technical solutions described herein facilitate stratification of the subject based on the transdermal analysis of the sample. For example, the cardiac monitoring device detects an occlusion in the coronary artery by analyzing the blood flowing the coronary artery. The cardiac monitoring device detects the occlusion based on presence of one or more cardiac biomarkers, such as the proteins troponin I (cTnI), fatty acid binding protein (FABP3), and the like. In one or more examples, the cardiac monitoring device determines the occlusion using an optical sensor. For example, the cardiac monitoring device deems the existence of the occlusion based on the biomarkers being within particular predetermined spectral ranges associated with the biomarker being detected. In one or more examples, a particular concentration or a particular amount of the cardiac biomarker(s) is indicative of the occlusion. The occlusion can be a symptom of the obstructive coronary artery disease. For example, the particular concentration or the particular amount of cardiac biomarker(s) are monitored, which is indicative of cardiac myocyte injury. Such a cardiac myocyte injury can be caused due to obstruction to blood flow in the coronary vasculature. Such obstruction reduces the supply of oxygen and nutrients to these cells, thus transitioning the cell from an oxidative to a non-oxidative state affecting the sustenance of structural proteins such as troponins and transport proteins like FABP3. Diminished metabolic activity can lead to a wakened cell membrane, thereby facilitating the release of these proteins in the circulation, which are then detected by the technical solutions described herein.

Further, the cardiac monitoring device, in one or more examples, determines a concentration of the biomarker(s) that are detected in the predetermined spectral range(s). Alternatively, or in addition, an amount of the biomarker(s) in the predetermined spectral range(s) is determined. The concentration (or amount) is used to stratify the subject into one of a predetermined categories. For example, the categories can include serious occlusion, medium occlusion, mild occlusion, and the like. It is understood that the categories listed herein are just few examples and that in one or more implementations of the technical solutions described herein, the categories can have different names. Additionally, there can be a different number of categories than those listed herein.

Figure 1:
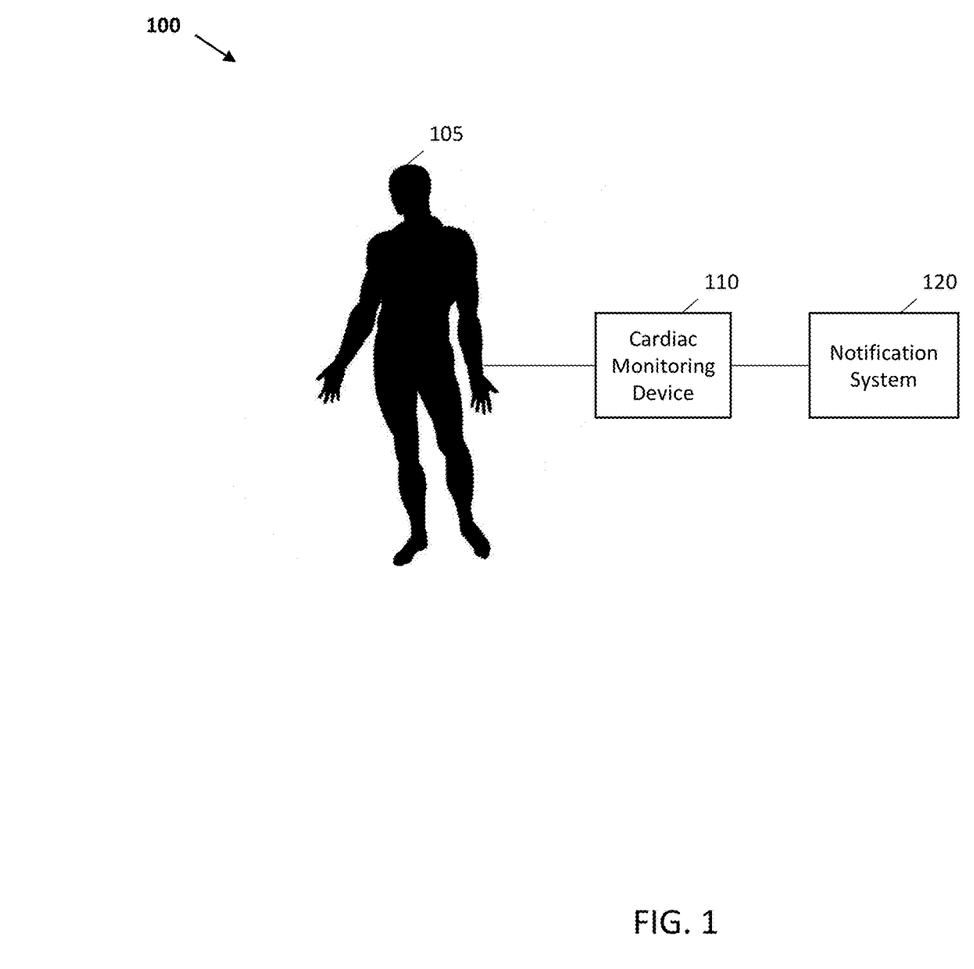
FIG. 1 depicts a block diagram of a system of optical detection of an occlusion in a cardiovascular system of a user according to one or more embodiments of the present invention.

FIG. 1 depicts a block diagram for a system that includes the cardiac monitoring device for analyzing the subject according to one or more embodiments of the present invention. The system 100 includes, among other components that are not shown, a subject 105 (or user), a cardiac monitoring device 110, and a notification system 120. The subject 105 is a human user who is being analyzed to predict if the subject 105 has an impending cardiac problem. The cardiac monitoring device 110 can analyze the subject 105 by analyzing body fluids of the subject 105.

The cardiac monitoring device 110 is coupled with a notification system 120. The notification system 120 can be coupled with the cardiac monitoring system 110 in a wired or a wireless manner. For example, the cardiac monitoring device 110 sends signals to the notification system 120 using communication protocols such as BLUETOOTH™, NEAR FIELD COMMUNICATION (NFC™), INTERNET PROTOCOL™, Ethernet, and the like. The notification system 120 can be a computer, such as a server computer, a desktop computer, a phone, or any other device that can provide an electronic communication. It should be noted that although the notification system 120 is shown separate, in one or more examples, the notification system 120 can be a part of the cardiac monitoring device 110 itself.

The notification system 120 provides a notification to the subject 105. Alternatively, or in addition, the notification system 120 provides a notification to a medical professional, such as a doctor, a nurse, a first responder, and the like. Further yet, the notification system 120 sends a notification to any other contact person that can be configured in the notification system 120.

The cardiac monitoring device 110 can be a wearable device that the subject 105 wears. Accordingly, in one or more examples, the cardiac monitoring device 110 can have one or more straps (not shown) to attach the cardiac monitoring device 110 to the subject 105. Alternatively, or in addition, the cardiac monitoring device 110 can be embedded in a dressing item, such as a shirt, an underwear, a vest, and the like.

Alternatively, or in addition, the cardiac monitoring device 110 is separate from the body of the subject 105, and the cardiac monitoring device 110 performs a transdermal analysis of the body fluids of the subject 105 by placing the cardiac monitoring device 110 and the subject 105 in contact with each other. For example, the subject 105 places a part of his/her body adjacent to the cardiac monitoring device 110. Alternatively, or in addition, the cardiac monitoring device 110 is placed on the subject's 105 body, for example, on the subject's 105 chest.

Figure 2:
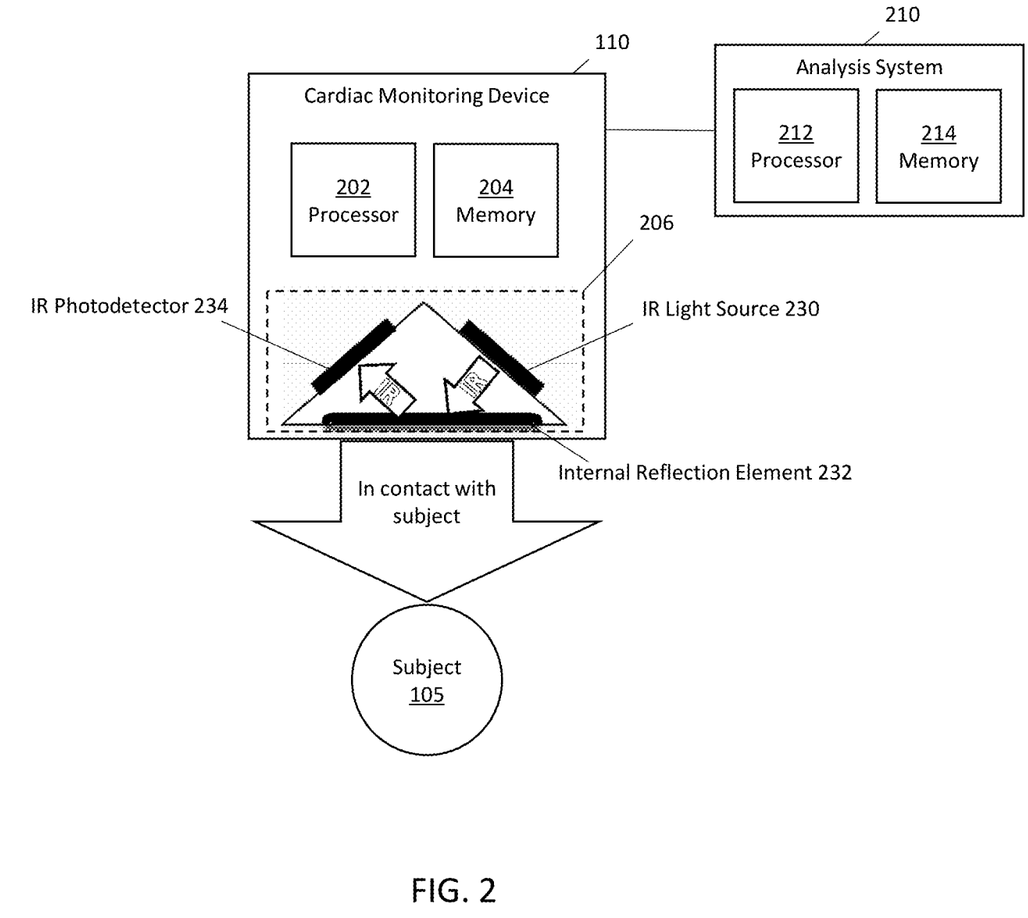
FIG. 2 depicts a block diagram of a cardiac monitoring device for transdermal optical monitoring of a biofluid according to one or more embodiments of the present invention.

FIG. 2 depicts the cardiac monitoring device 110 according to one or more embodiments of the present invention. The cardiac monitoring device 110 includes a processing unit 202, a memory 204, and a sensor 206. It should be noted that although one each of the processing unit 202, the memory 204, and the sensor 206 are shown, in one or more examples, the cardiac monitoring device 110 can include multiple of one or more of those components. In addition, the cardiac monitoring device 110 can include other components such as connectors, communication devices, and the like, which are not shown.

The processing unit 202 can include one or more processors, such as a microprocessor, that can execute on or more computer executable instructions. The memory 204 is a volatile and/or non-volatile memory device that can store the computer executable instructions in addition to data items such as media, text, databases, data structures, files, and other electronic data that facilitates the operation of the cardiac monitoring device 110.

The sensor 206 is coupled with the processing unit 202 so that the processing unit 202 receives one or more sensor signals from the sensor 206. In one or more examples, the processing unit 202 sends instructions to the sensor 206, for example, to trigger the operation of the sensor 206.

In one or more examples, the sensor 206 is an optical sensor that scans the body fluid of the subject 105. The cardiac monitoring device 110 is in contact with the subject 105, for example, in contact with the skin of the subject 105, to facilitate the scanning by the sensor 206.

The optical sensor transdermally detects one or more predetermined biomarkers, such as proteins or other types of chemicals in the human body, for example, in the blood flow and interstitial fluids. The optical sensors can be in addition to other types of sensors in the cardiac monitoring device 110. For example, the cardiac monitoring device 110 can further include sensors such as ECG sensors, haptic sensors, audio sensors, biosensors, and other types of sensors. The sensors can be placed at particular positions to measure the respective parameters of the subject 105. The sensors are placed in a specific configuration to facilitate receiving multiple measurement signals in parallel. In one or more examples, the cardiac monitoring device 110 is used for detection of progression of the obstructive coronary artery disease as described herein.

In one or more examples, the data from the sensors is transmitted in the form of electronic signals to an analysis system 210. The transmitted data includes the respective measurement signals from the one or more sensors, including the sensor 206. In one or more examples, the data is transmitted as streaming data. The electronic signals transmitted can be analog signals in one or more examples. Alternatively, or in addition, the electronic signals can include digital signals. Further, in one or more examples, the streaming data includes separate electronic signals from each of the multiple sensors that are embedded in the cardiac monitoring device 110. For example, the streaming data can include 7 ECG sensor signals and one or more biomarker sensor signals from the optical sensor 206. Other combinations of sensor signals is also possible in other embodiments. In one or more examples, the analysis system 210, based on the sensor signals, can determine indication of progression of the obstructive coronary artery disease, for example, using machine learning and/or other techniques. The analysis system 210, in such cases, sends a command/request to the notification system 120 to trigger the notification(s). It should be noted that although the analysis system 210 is shown separate from the cardiac monitoring device 110, in one or more examples, the analysis system 210 can be part of the cardiac monitoring device 110 itself.

In the cases where the analysis system 210 is separate from the cardiac monitoring device 110, the analysis system 210 can be a computing device, such as a server computer, a desktop computer, a laptop computer, a tablet computer, a phone, or any other such electronic device that includes a processing unit 212 and a memory 214. The processing unit 212 includes one or more processors that execute computer executable instructions. The memory 214 includes volatile/non-volatile memory device that facilitates the execution of the computer executable instructions. In one or more examples, the memory 214 stores the computer executable instructions. Further, the memory 214 can include media, text, databases, data structures, files, and other such electronic data to facilitate the execution of the computer executable instructions.

In one or more examples, to facilitate the scanning by the cardiac monitoring device 110, the optical sensor 206 is located in a predetermined vicinity positioned proximal to the aortic arch of the subject's 105 heart. The optical sensor signal is used to detect leakage of particular proteins/chemicals from the subject's heart during a myocardial injury state. For example, the detection can be used to improve accuracy of detecting the progression of obstructive coronary artery disease using other sensor signals, such as ECG signal. Alternatively, or in addition, the detection using the optical sensor signal can be used by itself. The detection of the leakage can be performed based on biomarkers using electromagnetic excitation and detection using optical filters. For example, the optical sensor 206 is used to detect chemicals/proteins that affect, or are released as a result of changes in the metabolic homeostasis. The combination of such chemicals/proteins are indicative of a progression of obstructive coronary artery disease, in combination with the ECG sensor signals.

For example, particular proteins such as Troponin and CK-MB, are used as biomarkers for MI. Further, Heart type Fatty Acid Binding Protein (H-FABP or FABP3) is also used as an early biomarker, and which is released in incremental amounts in the blood as early as 2 hours after an MI and consequently subsides after 6 hours. Using the optical sensor 206 to detect such protein(s) facilitates high sensitivity and specificity in the early detection of MI and reinfarction.

In one or more examples, the optical sensor 206 uses spectroscopy such as in near, mid, and far-infrared range, microwave range, visible region, or other such range of the electromagnetic spectrum. The range can be varied based on the protein/chemical being detected. The optical sensor 206 uses infrared (IR) spectroscopy that provides an optical fingerprint of the biomarker when scanned in the 2000 to 800 cm-1 (5 μm to 12.5 μm) range. This detection can be used to identify, differentiate and quantify the amount of the biomarkers (for example, troponin I, FABP3) in whole blood. The fingerprint for a biomarker can be a unique combination of absorbance peaks within a spectral range in which the concentration of the biomarker in a biofluid can be detected using the optical sensor 206. Absorbance peaks are monitored based on amplitude of the reflected light that is absorbed by a photodetector in the optical sensor 206 in one or more examples.

In one or more examples, the optical sensor 206 includes at least the following components: an IR light source 230, an internal reflection element (IRE) 232 and an IR photodetector 234.

The IR source 230 can include lasers, light emitting diodes (LEDs), radiative light sources, or other such sources of IR light. For detecting particular biomarkers one or more absorbance peaks may be identified at predetermined wavelengths of the IR light. For example, two absorbance wavelength ranges, 5.5 to 6.6 μm and 8.3 to 11.8 μm are sensitive and specific to FABP3 in whole blood. Further, three absorbance wavelength ranges for troponin in whole blood are 5.5 μm to 7.8 μm, 8.8 μm to 10.3 μm, and 10.5 to 12 μm. The IR source 230 uses such predetermined wavelengths to facilitate detection of the corresponding biomarkers. It is understood that the above described values are examples and that in one or more examples, different and/or additional wavelengths and/or ranges can be used. In one or more examples, the IR light source 230 transmits IR light of a particular wavelength based on a voltage that is applied to the IR light source 230. The voltage being applied to the IR light source 230 can be controlled by the processing unit 202, in one or more examples. The processing unit 202 applies a particular voltage depending on the biomarker that is being detected by the processing unit 202.

The IRE 232 can be made of particular material to facilitate the optical sensor 206 to detect the biomarker(s). For example, the IRE 232 can be made of low density polyethylene, diamond, ZnSe, Ge, Si etc. The IRE 232 is formed such that the IR light from the IR light source 230 is incident at an angle equal to or lesser than the critical angle associated with the IRE material to allow total internal reflection of the IR light. The critical angle is dependent on the material of the IRE 232. Further, the refractive indices of the IRE 232 and of the sample being analyzed, coupled with the wavelength of IR light dictate the penetration depth of the IR light into the tissue, blood (or any other body fluid) of the subject 105.

The IR photodetector 234 can include quantum wells, quantum dots, bolometers, and the like. The IR photodetector 234 is paired (maximum sensitivity) with the IR light source 230. In one or more examples, the IR photodetector 234 generates a voltage or an electric current as an output signal, which is proportional to an amount of light absorbed by the IR photodetector 234. The IR photodetector 234 is arranged so that the IR light reflected by the IRE 232 (and the subject 105) is incident upon the IR photodetector 234. The IR photodetector 234 accordingly provides absorption measurements of the IR light from the body fluid(s) of the subject 105. The processing unit 202, and or the analysis system 210 detects whether a biomarker is present in the subject 105 based on the absorption measurement. The processing unit 202 and/or the analysis system 210 further can stratify the subject 105 based on the absorption measurement.

It is understood that other optical components and filters such as notch filters (selective wavelength) and polarizers are also used by the optical sensor 206 to improve the selectivity and sensitivity of the optical sensor 206 when detecting the biomarker. Such components are not shown in the drawings.

After the IR light totally and internally reflects at the IRE contact surface, the IR light is detected by the IR photodetector 234. The signals before and after the IRE 232 makes contact with the skin are differentially processed to get the optical characteristics of the body fluid of the subject 105, for example, blood/interstitial fluid interrogated through the skin. The optical characteristics of the blood/interstitial fluid are analyzed to detect the presence of the biomarker which can serve as an indicator of a progression of obstructive coronary artery disease. It should be noted that the body fluid is analyzed dynamically during the body fluid being transported by the subject's 105 body. For example, the analysis is performed on blood as it flows through the coronary artery.

In one or more examples, when used in combination with other types of sensors that detect progression of the obstructive coronary artery disease, the absorption measurements from the optical sensor 206 can be used as validation for the results based on the other sensors, or vice versa.

It should be noted that although the examples described herein refer to using the optical sensor 206 for detecting biomarkers in blood that is flowing in a blood vessel in a body of a user, the techniques described herein can be used in other cases. For example, the techniques herein can be used for detecting the biomarkers in fluids that are collected in a bag or other type of container, other body fluid(s) in the body, or other types of material, such as tissues, blood, serum, cells etc. Further, it should be noted that although the examples herein describe detecting FABP3 and troponin I (cTnI) as the cardiac biomarkers for detecting progression of the obstructive coronary artery disease or other cardiac issue with the subject, in other examples, different cardiac biomarkers can be detected using the techniques described herein. Further yet, it should be noted that the techniques herein can be used for detecting biomarkers other than for detection of progression of the obstructive coronary artery disease. For example, the techniques may be used for detecting biomarker(s) for kidney failure, liver failure, or failure of any other organ in the subject's 105 body other than the heart.

Figure 3:
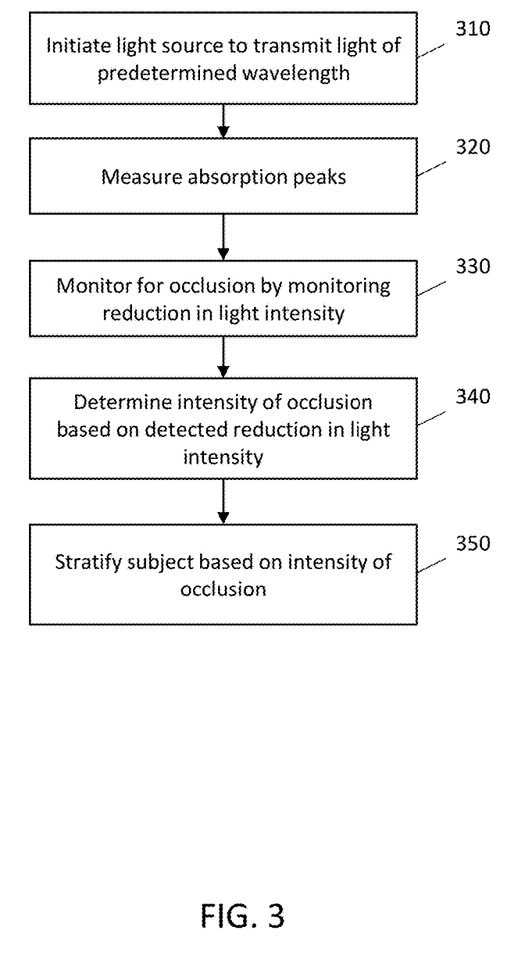
FIG. 3 depicts a flowchart of a method for detecting an occlusion in a biofluid vessel of a user according to one or more embodiments of the present invention.

FIG. 3 depicts a flowchart of a method 300 for optical detection of biomarkers in biofluids according to one or more embodiments of the present invention. The method 300 includes initiating the IR light source 230 to transmit light of a predetermined wavelength with the help of optical filters, at block 310. The processing unit 202 can initiate the IR light source 230 by causing a corresponding voltage being applied to the IR light source 230 to generate the light of the predetermined wavelength. The predetermined wavelength is based on a particular biomarker being detected. In one or more examples, the light emission is initiated at a particular periodic frequency, such as every 30 seconds, every one minute, every 10 seconds, or any other such frequency.

Further, the method 300 includes measuring one or more absorption peaks using the IR photodetector 234, at block 320. The absorption peaks that are measured are from the IR light reflected by the IRE 232, the reflected light being representative of a surface of the material being analyzed, which is in contact with the IRE 232. It should be noted that the material being analyzed here is the biofluid in the subject's 105 body via the skin (epidermis) where the subject 105 is in contact with the cardiac monitoring device 110. For example, the biofluid is blood in the coronary artery, the cardiac monitoring device 110 being in contact at a position adjacent to the coronary artery of the subject 105.

The method 300 further includes detecting a change in intensity of the reflected light, at block 330. The processing unit 202 detects the change in the intensity based on the output signal from the IR photodetector 234. The change can be detected based on the measurement of amplitude of the reflected light that is absorbed by the IR photodetector 234 being lesser than an expected measurement. Alternatively, or in addition, the change is a difference between the measured absorption amplitude and a predetermined value for the specific biomarker at the particular wavelength of IR light being transmitted by the IR light source 230. In one or more examples, when the difference is at least a predetermined value, the intensity of the received light is deemed to have reduced. The reduction in the intensity is proportional to an increase in concentration of the biomarker in the biofluid that is being scanned by the cardiac monitoring device 110. An increase in the biomarker is indicative of an occlusion in the vessel, for example, the coronary artery, of the biofluid.

Further, the method 300 includes determining a level of obstruction caused by the occlusion based on the intensity of the reflected light, at block 340. In one or more examples, the level of obstruction is mapped to the detected absorption measurements. For example, if the change in the absorption measurement is within a particular range, the level of obstruction is determined as a predetermined category that is mapped to the particular range. For example, the level of obstruction may be determined as a mild occlusion, mid occlusion, high occlusion. Other categories of levels of the obstruction are possible in other examples. In one or more examples, a combination of biomarkers is used to detect the occlusion and the level of the obstruction. For example, a change in concentrations (or amounts) of multiple biomarkers is detected and a change in the combination of biomarkers is used to determine the level of obstruction. For example, a combination of troponin I (cTnI) and FABP3 is used in one or more examples.

The method 300 further includes stratifying the subject 105 based on the level of obstruction that is detected, at block 350. For example, if the level of obstruction is deemed to be a mild occlusion, the subject 105 may be stratified as requiring a further examination. In case of a high occlusion, a percutaneous coronary intervention (PCI) or a coronary artery bypass graft (CABG) may be prescribed. Other stratification is possible in other examples based on the level of obstruction that is detected.

The one or more technical solutions described herein accordingly facilitate using optical sensors to detect particular proteins in a material, such as blood flowing inside a blood vessel, the detection performed in real time. In one or more examples, the technical solutions described herein facilitate detecting leakage of proteins/chemicals from the user's heart during an MI event to further improve accuracy of detecting progression of the obstructive coronary artery disease. Accordingly, the technical solutions improve existing techniques of detecting an occurrence of a heart attack. Further, the technical solutions herein are non-invasive and can be worn by a user as part of a clothing or other wearable device.

Figure 4:
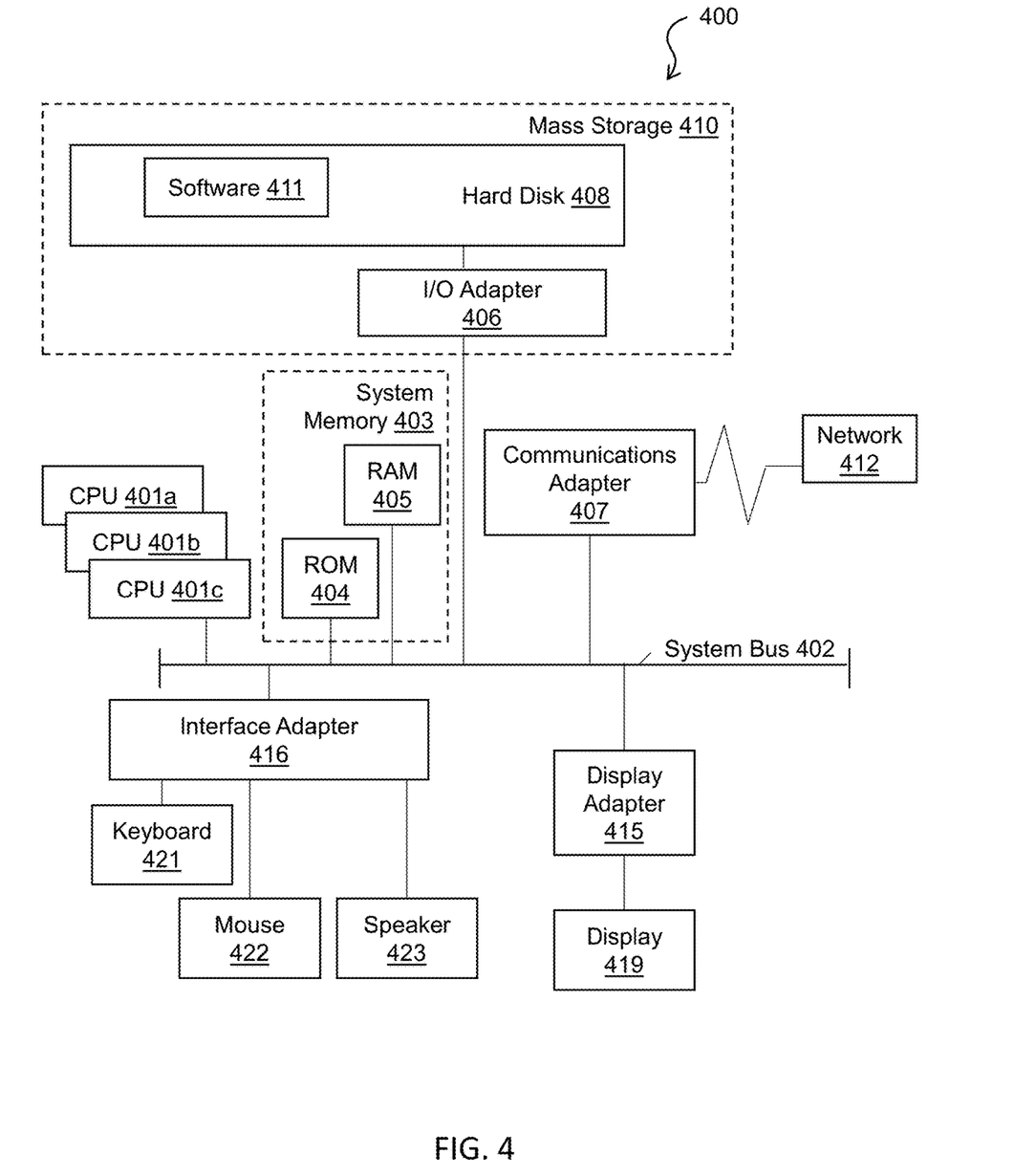
FIG. 4 depicts an example computer system that implements one or more embodiments of the present invention.

Turning now to FIG. 4, a computer system 400 is generally shown in accordance with an embodiment. The computer system 400 can be an electronic, computer framework comprising and/or employing any number and combination of computing devices and networks utilizing various communication technologies, as described herein. The computer system 400 can be easily scalable, extensible, and modular, with the ability to change to different services or reconfigure some features independently of others. The computer system 400 may be, for example, a server, desktop computer, laptop computer, tablet computer, or smartphone. In some examples, computer system 400 may be a cloud computing node. Computer system 400 may be described in the general context of computer system executable instructions, such as program modules, being executed by a computer system. Generally, program modules may include routines, programs, objects, components, logic, data structures, and so on that perform particular tasks or implement particular abstract data types. Computer system 400 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, the computer system 400 has one or more central processing units (CPU(s)) 401a, 401b, 401c, etc. (collectively or generically referred to as processor(s) 401). The processors 401 can be a single-core processor, multi-core processor, computing cluster, or any number of other configurations. The processors 401, also referred to as processing circuits, are coupled via a system bus 402 to a system memory 403 and various other components. The system memory 403 can include a read only memory (ROM) 404 and a random access memory (RAM) 405. The ROM 404 is coupled to the system bus 402 and may include a basic input/output system (BIOS), which controls certain basic functions of the computer system 400. The RAM is read-write memory coupled to the system bus 402 for use by the processors 401. The system memory 403 provides temporary memory space for operations of said instructions during operation. The system memory 403 can include random access memory (RAM), read only memory, flash memory, or any other suitable memory systems.

The computer system 400 comprises an input/output (I/O) adapter 406 and a communications adapter 407 coupled to the system bus 402. The I/O adapter 406 may be a small computer system interface (SCSI) adapter that communicates with a hard disk 408 and/or any other similar component. The I/O adapter 406 and the hard disk 408 are collectively referred to herein as a mass storage 410.

Software 411 for execution on the computer system 400 may be stored in the mass storage 410. The mass storage 410 is an example of a tangible storage medium readable by the processors 401, where the software 411 is stored as instructions for execution by the processors 401 to cause the computer system 400 to operate, such as is described herein below with respect to the various Figures. Examples of computer program product and the execution of such instruction is discussed herein in more detail. The communications adapter 407 interconnects the system bus 402 with a network 412, which may be an outside network, enabling the computer system 400 to communicate with other such systems. In one embodiment, a portion of the system memory 403 and the mass storage 410 collectively store an operating system, which may be any appropriate operating system, such as the z/OS or AIX operating system from IBM Corporation, to coordinate the functions of the various components shown in FIG. 4.

Additional input/output devices are shown as connected to the system bus 402 via a display adapter 415 and an interface adapter 416 and. In one embodiment, the adapters 406, 407, 415, and 416 may be connected to one or more I/O buses that are connected to the system bus 402 via an intermediate bus bridge (not shown). A display 419 (e.g., a screen or a display monitor) is connected to the system bus 402 by a display adapter 415, which may include a graphics controller to improve the performance of graphics intensive applications and a video controller. A keyboard 421, a mouse 422, a speaker 423, etc. can be interconnected to the system bus 402 via the interface adapter 416, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 4, the computer system 400 includes processing capability in the form of the processors 401, and, storage capability including the system memory 403 and the mass storage 410, input means such as the keyboard 421 and the mouse 422, and output capability including the speaker 423 and the display 419.

In some embodiments, the communications adapter 407 can transmit data using any suitable interface or protocol, such as the internet small computer system interface, among others. The network 412 may be a cellular network, a radio network, a wide area network (WAN), a local area network (LAN), or the Internet, among others. An external computing device may connect to the computer system 400 through the network 412. In some examples, an external computing device may be an external webserver or a cloud computing node.

It is to be understood that the block diagram of FIG. 4 is not intended to indicate that the computer system 400 is to include all of the components shown in FIG. 4. Rather, the computer system 400 can include any appropriate fewer or additional components not illustrated in FIG. 4 (e.g., additional memory components, embedded controllers, modules, additional network interfaces, etc.). Further, the embodiments described herein with respect to computer system 400 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

The present technical solutions may be a system, a method, and/or a computer program product at any possible technical detail level of integration. The computer program product may include a computer readable storage medium (or media) having computer readable program instructions thereon for causing a processor to carry out aspects of the present technical solutions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technical solutions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present technical solutions.

Aspects of the present technical solutions are described herein with reference to flowchart illustrations and/or block diagrams of methods, apparatus (systems), and computer program products according to embodiments of the technical solutions. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present technical solutions. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based based systems that perform the specified functions or acts or carry out combinations of special purpose hardware and computer instructions.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are to be construed in the broadest sense, superseding any other implied definitions hereinbefore or hereinafter unless expressly asserted to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

It will also be appreciated that any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Such computer storage media may be part of the device or accessible or connectable thereto. Any application or module herein described may be implemented using computer readable/executable instructions that may be stored or otherwise held by such computer readable media.

The descriptions of the various embodiments of the technical features herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A system comprising:
   an optical sensor comprising:
      a light source configured to emit infrared light in a predetermined spectral range;
      an internal reflection element that causes total internal reflection of the infrared light emitted by the light source, the total internal reflection causing an evanescent light to be produced on an opposite side of the reflecting surface;
      a photodetector that measures the total internal reflection, wherein the light source and the photodetector are both arranged on a same side of the internal reflection element; and
   a controller coupled with the optical sensor to receive a sensor signal from the optical sensor, the controller configured to:
      determine a first amount of light detected by the photodetector in response to an amount of light emitted by the light source and in response to the optical sensor not being in contact with a subject;
      determine a second amount of light detected by the photodetector in response to the amount of light emitted by the light source and in response to the optical sensor being in contact with the subject in a transdermal manner;
      detect a predetermined biomarker in a biofluid or biological tissue of the subject that is being monitored by the optical sensor in a non-invasive manner, the predetermined biomarker detected based on an amount of the evanescent light that is absorbed by the predetermined biomarker, the evanescent light that is absorbed by the predetermined biomarker is determined based on the first amount of light, and the second amount of light; and
      reporting a concentration of the predetermined biomarker based on the amount of evanescent light absorbed by the predetermined biomarker.

2. The system of claim 1, wherein the subject is deemed to have an occlusion in response to the concentration of the predetermined biomarker being above a predetermined threshold.

3. The system of claim 1, wherein the predetermined biomarker is troponin I (cTnI).

4. The system of claim 3, wherein the predetermined spectral range is 5.5 µm to 7.8 µm and 8.8 µm to 10.3 µm and 10.5 to 12 µm.

5. The system of claim 1, wherein the predetermined biomarker is fatty acid binding protein-3 (FABP3).

6. The system of claim 5, wherein the predetermined spectral range is 5.5 µm to 6.6 µm and 8.3 µm to 11.8 µm.

7. The system of claim 1, wherein the predetermined biomarker is a combination of proteins that comprises troponin I (cTnI) and fatty acid binding protein-3 (FABP3).

8. The system of claim 2, wherein the controller is further configured to determine a level of obstruction caused by the occlusion based on the concentration of the predetermined biomarker.

9. The system of claim 8, wherein the controller is further configured to stratify the predetermined biomarker based on the level of obstruction.

10. The system of claim 1, wherein detection of the predetermined biomarker comprises:
   generating, by the light source, the infrared light in the predetermined spectral range corresponding to the predetermined biomarker; and
   measuring, by the photodetector, absorption peaks in the total internal reflection; and
   comparing, by the controller, the absorption peaks in the first amount of light and the second amount of light in the predetermined spectral range.

11. A computer-implemented method for detecting an occlusion in a cardiovascular system of a user, the computer-implemented method comprising:
   generating a light within a predetermined spectral range, the light directed towards the cardiovascular system at a predetermined angle using an optical sensor that comprises:
      a light source configured to emit the light;
      an internal reflection element that reflects a first portion of the light, wherein a second portion of the light is absorbed by the user that is in contact with the internal reflection element; and
      a photodetector, wherein the light source and the photodetector are both arranged on a same side of the internal reflection element;
   detecting a concentration of a predetermined biomarker in a biofluid or biological tissue based on an amplitude of the light that is absorbed; and
   determining the occlusion in the cardiovascular system based on the concentration of the predetermined biomarker.

12. The computer-implemented method of claim 11, wherein the predetermined biomarker is troponin I (cTnI).

13. The computer-implemented method of claim 11, wherein the predetermined biomarker is fatty acid binding protein-3 (FABP3).

14. The computer-implemented method of claim 11, wherein the predetermined biomarker is a combination of proteins that comprises troponin I (cTnI) and fatty acid binding protein-3 (FABP3).

15. The computer-implemented method of claim 11, further comprising, determining level of obstruction caused by the occlusion based on the concentration of the predetermined biomarker.

16. The computer-implemented method of claim 15, further comprising, stratifying the user based on the level of obstruction.

17. A computer program product comprising a non-transitory memory having computer executable instructions stored thereon, the computer executable instructions when executed by a processing unit causes the processing unit to perform a method for quantification of a concentration of a predetermined biomarker, the method comprising:
   generating a light within a predetermined spectral range, the light directed towards a cardiovascular system at a predetermined angle using an optical sensor that comprises:
      a light source configured to emit the light;
      an internal reflection element that reflects a first portion of the light, wherein a second portion of the light is absorbed by a user that is in contact with the internal reflection element; and
      a photodetector, wherein the light source and the photodetector are both arranged on a same side of the internal reflection element;
   detecting a concentration of a predetermined biomarker in a biofluid or biological tissue based on an amplitude of the light that is absorbed; and
   determining an occlusion in the cardiovascular system based on the concentration of the predetermined biomarker.

18. The computer program product of claim 17, wherein the predetermined biomarker is at least one of troponin I (cTnI) and fatty acid binding protein-3 (FABP3).

19. The computer program product of claim 17, wherein the method further comprises, determining a level of obstruction caused by the occlusion based on the concentration of the predetermined biomarker.

20. The computer program product of claim 17, wherein the method further comprises stratifying the user based on the concentration of the predetermined biomarker.

* * * * *